(12) United States Patent
Ushio et al.

(10) Patent No.: US 7,138,140 B2
(45) Date of Patent: Nov. 21, 2006

(54) SUPLATAST TOSILATE CRYSTALS

(75) Inventors: Takanori Ushio, Saitama (JP); Hidenori Miura, Saitama (JP); Keiko Nagai, Gunma (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 489 days.

(21) Appl. No.: 10/297,601

(22) PCT Filed: Apr. 16, 2002

(86) PCT No.: PCT/JP02/03762

§ 371 (c)(1),
(2), (4) Date: Dec. 13, 2002

(87) PCT Pub. No.: WO02/083633

PCT Pub. Date: Oct. 24, 2002

(65) Prior Publication Data

US 2003/0149105 A1 Aug. 7, 2003

(30) Foreign Application Priority Data

Apr. 16, 2001 (JP) ............................. 2001-117165

(51) Int. Cl.
*A61K 9/14* (2006.01)
(52) U.S. Cl. .................................... 424/489
(58) Field of Classification Search ................ 424/489
See application file for complete search history.

(56) References Cited

U.S. PATENT DOCUMENTS

| | | | | |
|---|---|---|---|---|
| 4,556,737 A | * | 12/1985 | Koda et al. .................. | 564/218 |
| 5,475,033 A | * | 12/1995 | Ohmori et al. ............. | 514/599 |
| 5,478,942 A | * | 12/1995 | Himmelsbach et al. .. | 548/263.2 |
| 5,886,045 A | * | 3/1999 | Tokumochi et al. ........ | 514/599 |
| 5,965,565 A | * | 10/1999 | Chen et al. ................. | 514/278 |
| 6,329,428 B1 | * | 12/2001 | Yamauchi et al. .......... | 514/538 |

FOREIGN PATENT DOCUMENTS

| JP | 7-252213 | * | 10/1995 |
|---|---|---|---|
| JP | 7-300453 | | 11/1995 |
| JP | 11-315019 | | 11/1999 |

OTHER PUBLICATIONS

Takanori Ushio, Rui Tamura, Hiroki Takahashi, Nagao Azuma, and Keiji Yamamoto. Unusual Enantiomeric Resolution Phenomenon Observed Recrstallization of a Racemic Compound, 1996, VCH Verologsgesellschschaft mbh, Agnew.Chem. Int. Ed. Engl. 35 No. 20. pp. 2372-2374.*
Brittain, H. G. Pharmaceutical Sciences: Polymorphism in Pharmaceutical Solids. vol. 95, 1995 Marcel Dekker, p. 236.*
Takanori Ushio et al.: "Unusual enantiomeric resolution phenomenon observed upon recrystallization ofa racemic compound" Angew. Chem. Int. Ed. Engl., vol. 35, pp. 2372-2374 1996.
Kagaku, vol. 54, No. 6, pp. 47-54 1999 with English abstract.

* cited by examiner

*Primary Examiner*—Michael P. Woodward
*Assistant Examiner*—Marc C. Fitzgerald
(74) *Attorney, Agent, or Firm*—Oblon, Spivak, McClelland, Maier & Neustadt, P.C.

(57) ABSTRACT

Provided are a suplatast tosilate crystal showing characteristic peaks in powder X-ray diffraction diffraction angles (2θ±0.1°) of 5.6°, 9.0°, 11.0°, 15.3°, 16.5°, 17.2°, 17.9°, 19.2°, 19.9°, and 21.5°; and a preparation process of the crystal. Owing to merits such as fluctuation-free optically active substance ratio, low hygroscopicity and high storage stability, the suplatast tosilate crystal of the present invention can be mass-produced easily and, at the same time, is advantageous in drug preparation quality management. It is thus excellent as raw material for pharmaceuticals.

12 Claims, 4 Drawing Sheets

SUPLATAST TOSILATE CRYSTALS

TECHNICAL FIELD

The present invention relates to a novel suplatast tosilate crystal useful as an antiallergic agent or a medication for dysuria, and preparation process of the crystal.

BACKGROUND ART

Suplatast tosilate [(±)-[2-[4-(3-ethoxy-2-hydroxypropoxy) phenylcarbamoyl] ethyl] dimethylsulfonium p-toluenesulfonate] represented by the below-described formula has excellent inhibitory action against IgE antibody formation, is useful as a medication for various allergic diseases such as bronchial asthma, atopic dermatitis and allergic rhinitis and is utilized in the racemate as a pharmaceutical (refer to Japanese Patent Publication No. Hei 3-70698). It is also known that the suplatast tosilate is useful as a medication for dysuria or pruritus associated with kidney dialysis (WO 00/27383, Japanese Patent Laid-Open No. Hei 11-315019).

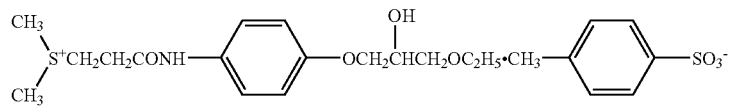

As the crystal of the racemate of the suplatast tosilate, those prepared by the process as described in Japanese Patent Publication No. Hei 3-70698 and Japanese Patent Laid-Open No. Hei 7-252213 (which crystals will hereinafter be called "first crystal" and "second crystal", respectively) are known.

The suplatast tosilate first crystal is however a peculiar compound, because its optically active substance ratio fluctuates when re-crystallized at a high concentration as described in Japanese Patent Laid-Open No. Hei 7-300453 or Angew, Chem. Int. Ed. Engl., 35, 2372–2374(1996). Adjustment of the optical active substance ratio within a predetermined range, thereby maintaining its quality as a pharmaceutical requires re-crystallizing operation at a lowered solution concentration, which needs a large amount of a solvent for re-crystallization. Moreover, since re-crystallization at a high concentration causes fluctuations in the optically active substance ratio, the crystal cannot be collected from a re-crystallized mother liquor and the whole amount of the mother liquor is inevitably discarded, which leads to a rise in the manufacturing cost. Another problem is that the crystal whose optically active substance ratio stands outside a predetermined range owing to fluctuations must be discarded. The reason why the first crystal suffers from fluctuations in the optically active substance ratio is not known clearly, but is presumed to owe to crystal growth at a portion undergoing a slight change in the ratio (Refer to, "Kagaku, 54; No. 6, 47–54 (1999)").

Moreover, high hygroscopicity of suplatast tosilate, both the first crystal and second crystal, disturbs easy handling during a quality test, storage management, or drug preparation step. Described specifically, the water content of the crystal increases during its preparation step, which may change its adhesion property, making it difficult to fill it in capsules or, from the viewpoint of quality management, may cause a drop in melting point owing to moisture absorption, making it nonconforming. It is therefore necessary to severely control the storage environment. The suplatast tosilate second crystal has not yet been developed as a pharmaceutical, because considerably high deliquescence makes it difficult to control its quality.

DISCLOSURE OF THE INVENTION

With the foregoing in view, the present inventors have carried out an extensive investigation. As a result, they have found a novel crystal form of suplatast tosilate not only having an X-ray diffraction pattern different from that of the conventional crystal form and being substantially free from fluctuations in the optically active substance ratio, but also having low hygroscopicity, being purified conveniently, and being excellent in both stability and handling ease can be prepared by crystallizing or re-crystallizing suplatast tosilate in a specific solvent, and completed the invention.

In one aspect of the present invention, there is thus provided a crystal form of suplatast tosilate (which may hereinafter be called "invention crystal") exhibiting characteristic peaks in powder X-ray diffraction at diffraction angles (2θ±0.1°) of 5.6°, 9.0°, 11.0°, 15.3°, 16.5°, 17.2°, 17.9°, 19.2°, 19.9° and 21.5°.

In another aspect of the present invention, there is also provided a process for preparing the above-described suplatast tosilate crystal, which comprises crystallizing or re-crystallizing suplatast tosilate from an acetone-water mixed solvent or a $C_{2-4}$ aliphatic alcohol-water mixed solvent.

In a further aspect of the present invention, there is also provided a pharmaceutical composition comprising the above-described suplatast tosilate crystal.

In a still further aspect of the present invention, there is also provided use of the above-described suplatast tosilate crystal for the preparation of a pharmaceutical composition.

In a still further aspect of the present invention, there is also provided a treating method of allergic diseases, dysuria or pruritus associated with kidney dialysis, which comprises administering an effective amount of the above-described suplatast tosilate crystal.

BEST MODE FOR CARRYING OUT THE INVENTION

The invention crystal is available by crystallizing or re-crystallizing suplatast tosilate (including the above-described first and second crystals) from an acetone-water mixed solvent or a $C_{2-4}$ aliphatic alcohol-water mixed solvent. Examples of the $C_{2-4}$ aliphatic alcohol include ethanol, propanol, 2-propanol and 2-butanol. From the viewpoints of ease of operation, uniformity of the optically active substance ratio and collection efficiency of the invention crystal, a mixed solvent of 2-propanol, 2-butanol or acetone with water is preferred among the above-described mixed solvents.

No particular limitation is imposed on the concentration of the solvent insofar as it does not cause fluctuations in an optically active substance ratio, permits dissolution under heating and permits formation of crystals when stored at a predetermined temperature. The concentration usually ranges from 10 to 70 W/V %, preferably from 15 to 60 W/V %, more preferably from 15 to 50 W/V %.

Although the water content in the mixed solvent can be selected as needed, depending on the nature of the organic solvent, it usually ranges from 0.3 to 15 V/V %, preferably from 0.5 to 12 V/V %, more preferably from 0.8 to 10 V/V %, particularly preferably from 1.5 to 3 V/V % in order to preferentially precipitate the invention crystal. Precipitation of the first crystal occurs without water, while the formation amount of the invention crystal markedly lowers at a water content exceeding 15 V/V %. It is therefore very important to control the water content within a predetermined range. Although the temperature upon dissolution of suplatast tosilate can be selected as needed, it usually ranges from 30 to 65° C., more preferably from 30 to 50° C. The storage temperature usually ranges from −50 to 30° C., preferably from −40 to 20° C., more preferably from −30 to 10° C. Upon storage at a predetermined temperature, an adequate amount of a suplatast tosilate crystal may be added as seed crystal for promoting crystallization. The amount of the seed crystal is usually 5 W/W % or less, preferably 3 W/W % or less, more preferably 1 W/W % or less based on the suplatast tosilate dissolved in the solvent. Upon storage at a predetermined temperature, the solution may be allowed to stand while stirring in order to shorten the crystallization time and to control particle size.

Figure 1:
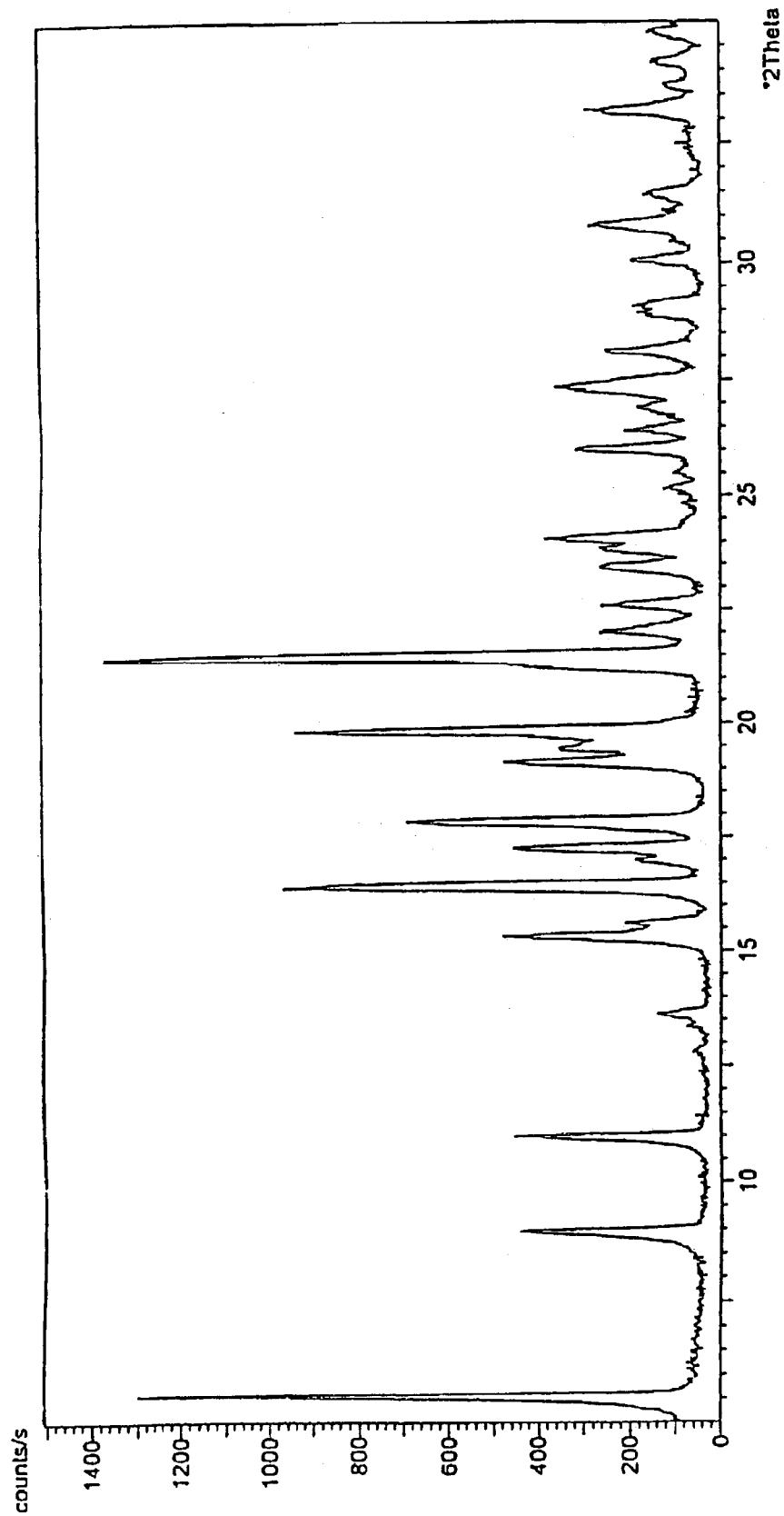
FIG. 1 is a powder X-ray diffraction pattern of the invention crystal of suplatast tosilate (Example 1) in which the ordinate describes the intensity of X-ray and the abscissa describes a diffraction angle (2θ).
Figure 2:
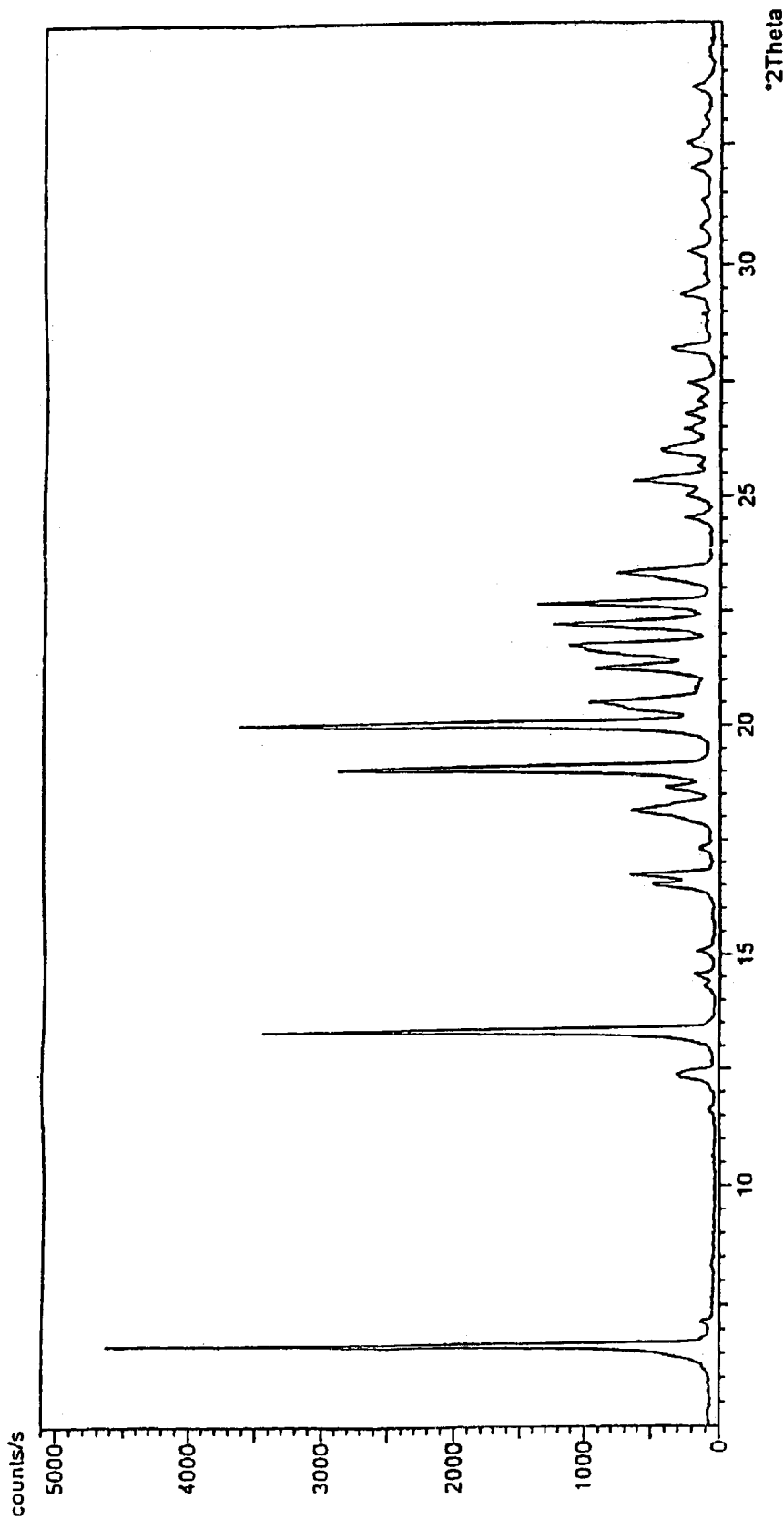
FIG. 2 is a powder X-ray diffraction pattern of suplatast tosilate first crystal (Comparative Example 1) in which the ordinate describes the intensity of X-ray and the abscissa describes a diffraction angle (2θ).
Figure 3:
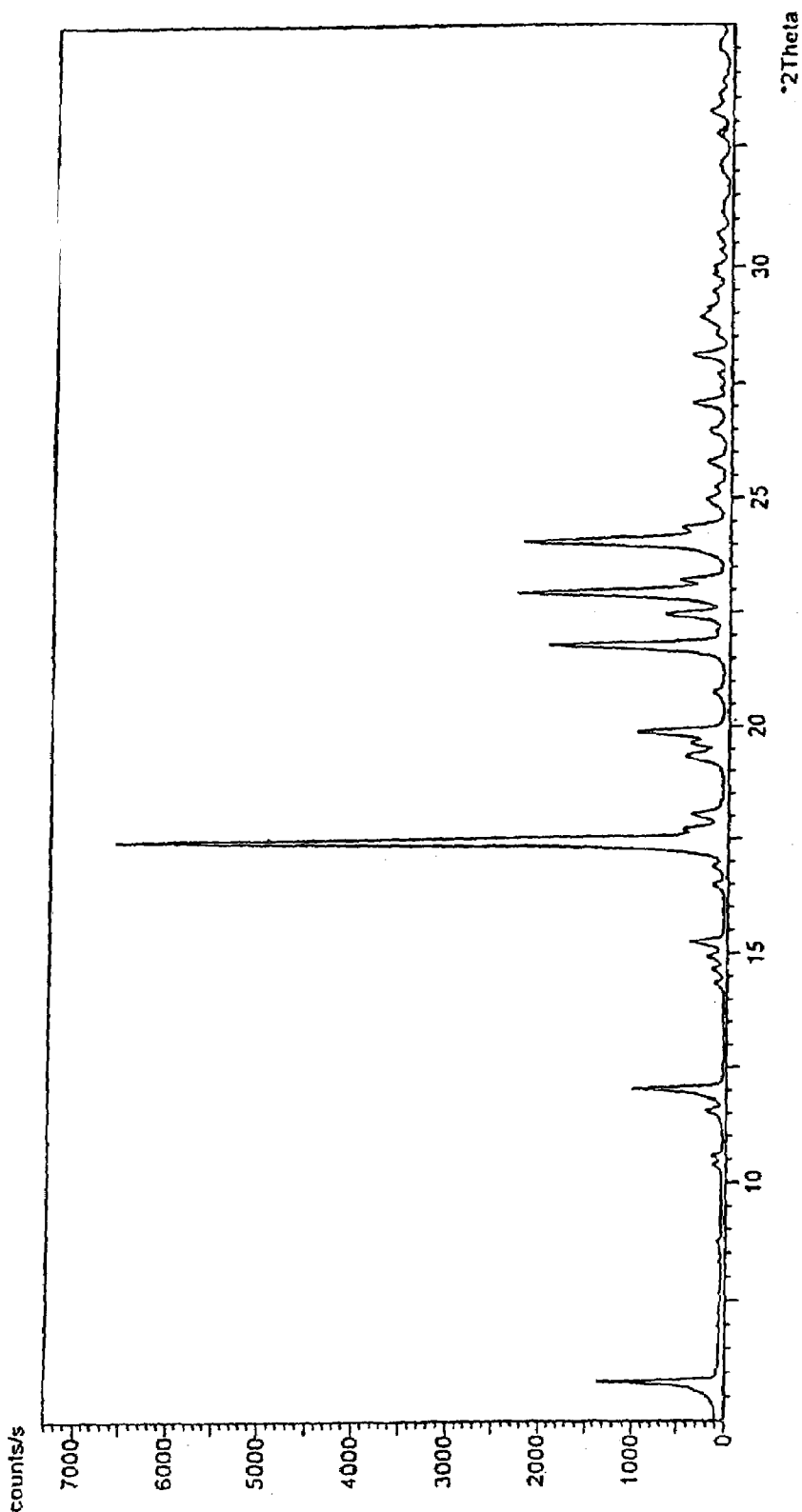
FIG. 3 is a powder X-ray diffraction pattern of suplatast tosilate second crystal (Comparative Example 4) in which the ordinate describes the intensity of X-ray and the abscissa describes a diffraction angle (2θ).

The powder X-ray diffraction pattern of the invention crystal thus obtained is as illustrated in FIG. 1. The crystal show characteristic peaks at diffraction angles (2θ+0.1°) of around 5.6°, 9.0°, 11.0°, 15.3°, 16.5°, 17.2°, 17.9°, 19.2°, 19.9° and 21.5°. On the other hand, the powder X-ray diffraction pattern of the first crystal is as illustrated in FIG. 2 and peaks are found at diffraction angles of around 6.7°, 13.3°, 19.0°, 20.0°, 21.7° and 22.6°. The powder X-ray diffraction pattern of the second crystal is as illustrated in FIG. 3 and peaks are found at diffraction angles of around 5.7°, 12.0°, 17.4°, 19.8°, 21.7°, 22.9° and 24.0°. The powder X-ray diffraction data were collected by exposing the crystal to CuKα radiation (1.541Å) in a Philips PW3050 X-ray Diffractometer and detecting peaks by a vertical goniometer.

The invention crystal can be prepared very easily from the ordinarily employed suplatast tosilate first crystal or second crystal. Its optically active substance ratio is almost fixed to 1.0 so that it can be recovered even from the mother liquor after re-crystallization and therefore does not have an adverse environmental effect; and compared with the conventional crystal, the amount of the solvent used upon re-crystallization can be reduced by half, which enables mass treatment. Moreover, since the invention crystal is free from fluctuations in the optically active substance ratio, it always meets the specification, which improves their recovery ratio.

In addition, the invention crystal is advantageous in quality management because of considerably high storage stability.

Moreover, the invention crystal having lower hygroscopicity than the conventional first or second crystal is therefore free from fluctuations in water content, or lowering in melting point or change in IR spectrum due to moisture absorption upon any step of preparation, quality test, storage management or drug preparation. It is not necessary to severely control the operation environment and in this sense, it is a crystal excellent in handling ease.

After pulverization or without pulverization, the suplatast tosilate crystal of the present invention can be formulated into pharmaceutical compositions in the various forms, for example, orally available formulations such as tablets, capsules, granules, fine granules, powders and dry syrups, and preparations for external use such as suppositories, inhalants, nose drops, ointments, plasters, and aerosols, and injections. These pharmaceutical compositions can be prepared in a manner known per se in the art by using a pharmacologically acceptable carrier. Orally administrable solid preparations such as tablets, coated tablets, granules, powders, dry syrups or capsules can be prepared by adding an excipient and if necessary, a binder, disintegrant, lubricant, colorant, taste corrigent and/or aroma corrigent to the effective ingredient and then treating the mixture in a conventional manner. Orally administrable liquid preparations such as liquid preparations for internal use or syrups can be prepared by adding a taste corrigent, buffer, stabilizer and/or aroma corrigent to the effective ingredient and then treating the resulting mixture in a conventional manner. Injections such as subcutaneous injection, intramuscular injection or intravenous injection can be prepared by adding a pH regulator, buffer, stabilizer, isotonizing agent and/or local anesthesia to an effective ingredient and then treating the mixture in a conventional manner. A rectal suppository can be prepared by adding an excipient to the effective ingredient and then adding thereto a surfactant if necessary, and then treating the resulting mixture in a conventional manner. An ointment in the form of a paste, cream or gel can be prepared by adding an ordinarily employed base, stabilizer, humectant and/or preservative according to need and then mixing them. Examples of the base include white petrolatum, paraffin, glycerin, cellulose derivatives, polyethylene glycol, silicon and bentonite. Examples of the preservative include methyl paraoxybenzoate, ethyl paraoxybenzoate, and propyl paraoxybenzoate. A plaster can be prepared by applying the above-described ointment, cream, gel or paste to an ordinarily employed support in a conventional manner. Examples of the support include woven fabrics of cotton, staple fiber or chemical fibers, nonwoven fabrics, and films or foamed sheets of soft polyvinyl chloride, polyethylene or polyurethane.

These pharmaceutical compositions are useful as a remedy for allergic diseases of human and other mammals such as bronchial asthma, atopic dermatitis and allergic rhinitis, dysuria or pruritus associated with the kidney dialysis (refer to Japanese Patent Publication No. Hei 3-70698, Wo 00/27383, Japanese Patent Laid-Open No. Hei 11-315019).

The pharmaceutical composition of the present invention is highly effective for treating or alleviating various symptoms of dysuria such as pollakiuria, incontinence, urodynia and cystalgia. In particular, the pharmaceutical composition of the present invention markedly alleviates the main symptoms of dysuria, more specifically, pollakiuria, urodynia and cystalgia, resulting from diseases related to the bladder or prostate, bladder cancer, or prostate cancer. Preferred examples of the causative disease include diseases of the bladder wall or occlusive diseases of the urinary tract such as acute or chronic cystitis, interstitial cystitis, hemorrhagic cystitis, radiation cystitis, vesical tuberculosis, vesical neck constriction, bladder cancer, acute or chronic prostatitis, prostatic cancer and prostatic hypertrophy, with acute or chronic cystitis, interstitial cystitis, hemorrhagic cystitis, radiation cystitis, vesical tuberculosis, bladder cancer, and acute or chronic prostatitis being particularly preferred. The pharmaceutical composition of the present invention is particularly effective for improving the urine volume discharged in a single urination, thereby alleviating pollakiuria, and for treating or ameliorating cystalgia.

When the pharmaceutical composition of the present invention contains, in addition to the suplatast tosilate crystal, a steroid drug, it has more improved therapeutic effects. Moreover, such combined use is desired also from the viewpoint of preventing side effects in the treatment of chronic cystitis, interstitial cystitis or chronic prostatitis, because the administration amount of the steroid drug can be proportionately reduced.

Although the amount of the suplatast tosilate crystal to be incorporated in the above-described pharmaceutical composition varies, depending on the symptom of a patient to whom the composition is administered, dosage form or the like, a preferred amount usually ranges from about 5 to 1000 mg in an orally administrable agent, from about 0.1 to 500 mg in an injection, and from about 5 to 1000 mg in a suppository or preparation for external use, each per unit dosage form. The daily dose of the suplatast tosilate crystals in the pharmaceutical composition also varies, depending on the symptom or the like so it cannot be determined in a wholesale manner, but about 0.1 to 5000 mg is preferred.

EXAMPLES

The present invention will hereinafter be described in further details by Examples. It should however be borne in mind that the present invention is not limited to or by them.

Example 1

To 24.0 g of suplatast tosilate first crystals were added 34.5 mL of acetone and 1.5 mL of water. The mixture was heated to 30° C. to dissolve the former in the latter, followed by cooling to about 5° C. Then, about 5 mg of suplatast tosilate first crystals were added as seed crystals and the mixture was stirred at the same temperature to cause precipitation. The crystals thus precipitated were filtered and dried to yield 16.24 g (recovery ratio: 67.7%) of suplatast tosilate crystals of the present invention. They had a melting point of 82.2° C. The results of powder X-ray diffraction of the crystals are shown in FIG. 1.

Example 2

To 2.0 g of suplatast tosilate first crystals were added 4.0 mL of 2-propanol and 0.2 mL of water. The mixture was heated to 40° C. to dissolve the former in the latter. After cooling to about 5° C., about 5 mg of suplatast tosilate first crystals were added as seed crystals. The mixture was allowed to stand at −20° C. to cause precipitation. The crystals thus precipitated were filtered and dried to yield 1.68 g (recovery ratio: 84.0%) of the suplatast tosilate crystals of the present invention. Their melting point was 82.3° C. The powder X-ray diffraction pattern of the resulting crystals was similar to that of the crystals of FIG. 1 and characteristic peaks were found at diffraction angles ($2\theta \pm 0.1°$) of 5.6°, 9.0°, 11.0°, 15.3°, 16.5°, 17.2°, 17.9°, 19.2°, 19.9° and 21.5°.

Example 3

To 2.0 g of suplatast tosilate first crystals were added 12.0 mL of acetone and 0.3 mL of water. The mixture was heated to 30° C. to dissolve the former in the latter. After cooling to about 5° C., about 5 mg of the suplatast tosilate first crystals were added as seed crystals. The mixture was allowed to stand at the same temperature to cause precipitation. The crystals thus precipitated were filtered and dried to yield 1.44 g (recovery ratio: 72.0%) of the suplatast tosilate crystals of the present invention. Their melting point was 83.3° C. The powder X-ray diffraction pattern of the resulting crystals was similar to that of the crystals of FIG. 1 and characteristic peaks were found at diffraction angles ($2\theta \pm 0.1°$) of 5.6°, 9.0°, 11.0°, 15.3°, 16.5°, 17.2°, 17.9°, 19.2°, 19.9° and 21.5°.

Example 4

To 1.0 g of suplatast tosilate first crystals were added 1.0 mL of ethanol and 0.1 mL of water. The mixture was heated to 40° C. to dissolve the former in the latter. After cooling to about 5° C., about 5 mg of the suplatast tosilate first crystals were added as seed crystals. The mixture was allowed to stand at −20° C. to cause precipitation. The crystals thus precipitated were filtered and dried to yield 0.89 g (recovery ratio: 89.0%) of the suplatast tosilate crystals of the present invention. Their melting point was 83.0° C. The powder X-ray diffraction pattern of the resulting crystals was similar to that of the crystals of FIG. 1 and characteristic peaks were found at diffraction angles ($2\theta \pm 0.1°$) of 5.6°, 9.0°, 11.0°, 15.3°, 16.5°, 17.2°, 17.9°, 19.2°, 19.9° and 21.5°.

Example 5

To 2.0 g of suplatast tosilate first crystals were added 4.0 mL of 2-butanol and 0.4 mL of water. The mixture was heated to 40° C. to dissolve the former in the latter. After cooling to about 5° C., about 5 mg of the suplatast tosilate first crystals were added as seed crystals. The mixture was allowed to stand at −20° C. to cause precipitation. The crystals thus precipitated were filtered and dried to yield 1.44 g (recovery ratio: 72.0%) of the suplatast tosilate crystals of the present invention. Their melting point was 82.3° C. The powder X-ray diffraction pattern of the resulting crystals was similar to that of the crystals of FIG. 1 and characteristic peaks were found at diffraction angles ($2\theta \pm 0.1°$) of 5.6°, 9.0°, 11.0°, 15.3°, 16.5°, 17.2°, 17.9°, 19.2°, 19.9° and 21.5°.

Example 6

To 10.0 g of suplatast tosilate first crystals were added 30 mL of acetone and 1 mL of water. The mixture was heated to 40° C. to dissolve the former in the latter. After cooling to about 5° C., about 5 mg of the suplatast tosilate first crystals were added as seed crystals. The mixture was allowed to stand at −20° C. to cause precipitation. The crystals thus precipitated were filtered and dried to yield 8.96 g (recovery ratio: 89.6%) of the suplatast tosilate crystals of the present invention. Their melting point was 81.9° C. The powder X-ray diffraction pattern of the resulting crystals was similar to that of the crystal of FIG. 1 and characteristic peaks were found at diffraction angles (2θ±0.1°) of 5.6°, 9.0°, 11.0°, 15.3°, 16.5°, 17.2°, 17.9°, 19.2°, 19.9° and 21.5°. The filtrate was distilled under reduced pressure to remove the solvent. To the residue were added 3 mL of acetone and 0.1 mL of water. The mixture was heated to 40° C. to dissolve the former in the latter. After cooling to about 5° C., about 3 mg of suplatast tosilate first crystals were added as seed crystals. The mixture was allowed to stand at −20° C. to cause precipitation. The crystals thus precipitated were filtered and dried, whereby 0.63 g (recovery ratio: 63.0%, total recovery ratio: 96%) of the suplatast tosilate crystals of the invention. The melting point was 82.1° C. The powder X-ray diffraction pattern of the crystals thus obtained was similar to that of FIG. 1 and characteristic peaks were found at diffraction angles (2θ±0.1°) of 5.6°, 9.0°, 11.0°, 15.3°, 16.5°, 17.2°, 17.9°, 19.2°, 19.9° and 21.5°. Both the crystals obtained by the first operation and those obtained by the second operation showed an optically active substance ratio around 1.00.

Comparative Example 1

To 1.0 g of suplatast tosilate first crystals was added 4.0 mL of 2-propanol. The mixture was heated to 40° C. to dissolve the former in the latter. After cooling to room temperature, about 5 mg of the suplatast tosilate first crystals were added as seed crystals. The mixture was allowed to stand at 5° C. to cause precipitation. The crystals thus precipitated were filtered and dried to yield 0.92 g (recovery ratio: 92.0%) of suplatast tosilate first crystals of Comparative Example 1. Its melting point was 87.5° C.

Comparative Example 2

To 2.0 g of suplatast tosilate first crystals was added 12 mL of ethanol. The mixture was heated to 40° C. to dissolve the former in the latter. After cooling to room temperature and addition of 12 mL of isopropyl ether, about 10 mg of the suplatast tosilate first crystals were added as seed crystals. The mixture was allowed to stand at 5° C. to cause precipitation. The crystals thus precipitated were filtered and dried to yield 1.82 g (recovery ratio: 91.0%) of suplatast tosilate first crystals of Comparative Example 2. Their melting point was 86.7° C.

Comparative Example 3

To 1.0 g of suplatast tosilate first crystals was added 1.0 mL of ethanol. The mixture was heated to 40° C. to dissolve the former in the latter. After cooling to about 5° C., about 2 mg of the suplatast tosilate first crystals were added as seed crystals. The mixture was allowed to stand at −20° C. to cause precipitation. The crystals thus precipitated were filtered and dried to yield 0.81 g (recovery ratio: 81.0%) of suplatast tosilate first crystals of Comparative Example 3. Their melting point was 87.1° C.

Comparative Example 4

To 10.0 g of suplatast tosilate first crystals was added 40 mL of 2-propanol. The mixture was heated to 70° C. to dissolve the former in the latter. After cooling to room temperature, about 20 mg of suplatast tosilate second crystals were added as seed crystals. The mixture was allowed to stand at 20° C. to cause precipitation. The crystals thus precipitated were filtered and dried to yield 9.32 g (recovery ratio: 93.2%) of the suplatast tosilate second crystal of Comparative Example 4. Their melting point was 81.7° C.

[Test 1] Measurement of an Optically Active Substance Ratio

The optically active substance ratio of each of the suplatast tosilate crystals of the present invention obtained in Examples 1 to 3, and the suplatast tosilate first crystals obtained in Comparative Examples 1 to 3 was measured using a chiral stationary phase column ("Chiralcel OD-H", 4.6 mm×25 cm, product of Daicel Chemical Industries) with n-hexane ethanol-trifluoroacetic acid-diethylamine (750:250:5:1) as a mobile phase. As a result, it has revealed that the first crystals undergo a change in the optically active substance ratio, while the invention crystal is free from a change in the optically active substance ratio.

TABLE 1

| Sample | Crystal form | Optically active substance ratio of suplatast tosilate ((+)/(−)) |
|---|---|---|
| Example 1 | Invention crystal | 1.00 |
| Example 2 | Invention crystal | 1.00 |
| Example 3 | Invention crystal | 1.00 |
| Comparative Example 1 | First crystal | 1.09 |
| Comparative Example 2 | First crystal | 0.97 |
| Comparative Example 3 | First crystal | 0.94 |

The optically active substance ratio of the suplatast tosilate in the mother liquor in each of Examples and Comparative Examples was measured as described above. The ratio in Example 1 to 6 was from 0.99 to 1.01, while it was 0.57 in Comparative Example 1, 0.87 in Comparative Example 2, and 0.42 in Comparative Example 3. Accordingly, the invention crystal can be recovered again from the mother liquor, while the first crystal cannot be recovered from the mother liquor. Such a phenomenon owes to optical enrichment phenomenon typically observed upon formation of the first crystal.

[Test 2] Hygroscopicity Test 1

In a dessicator (adjusted to 75% RH) having a saturated aqueous solution of sodium chloride charged therein, 1.0 g of each of the suplatast tosilate crystals of the invention obtained in Example 1, commercially available suplatast tosilate first crystals and the suplatast tosilate second crystals obtained in Comparative Example 4 were stored at 25° C. and a time-dependent weight change was measured.

Figure 4:
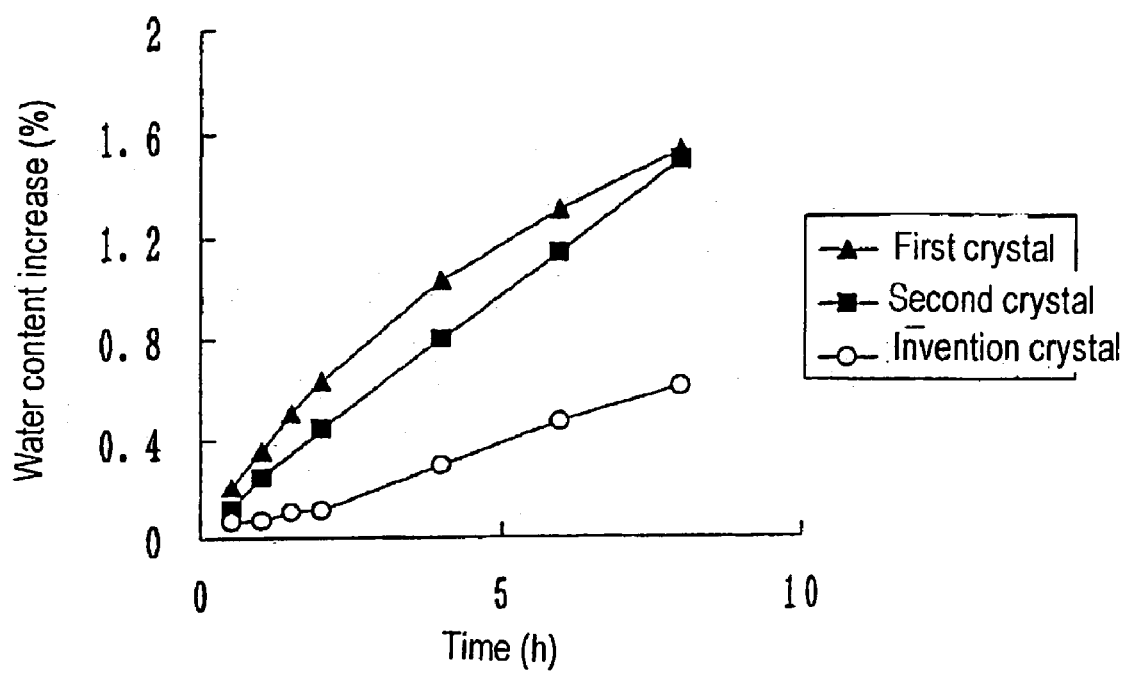
FIG. 4 is a graph illustrating a water content increase, at 25° C. and relative humidity of 75%, of the invention crystal of suplatast tosilate (Example 1) suplatast tosilate first crystal (commercially available product) and suplatast tosilate second crystal (Comparative Example 4).

As is apparent from FIG. 4, it has been understood that the invention crystal is excellent in handling ease upon any step of preparation, quality test, storage management, and drug preparation, because it has lower hygroscopicity than each of the first crystal and second crystal.

[Test 3] Hygroscopicity Test 2

Each of the suplatast tosilate crystals of the invention obtained in Example 1, and the second crystals obtained in accordance with the process of Comparative Example 4 (each, 0.5 g) were stored at 40° C. and relative humidity of 50% for 14 days, followed by observation of their appearance, powder X-ray diffraction and differential scanning calorimetry (DSC) in order to investigate storage stability. As a result, the invention crystal was almost free from a change in appearance, and also almost free from a change in powder X-ray diffraction peaks and in DSC. The second crystal showed deliquescence after storage for one week so that neither powder X-ray diffraction peaks nor DSC was measured.

[Test 4] Heat Stability Test

The invention crystals of suplatast tosilate obtained in accordance with the process of Example 1 and commercially available suplatast tosilate first crystals, each 3.6 g, were stored at 60° C. for 3 months in a glass air-tight container and the formation amount and powder X-ray diffraction of a decomposition product ((±)-4-(3-ethoxy-2-hydroxypropoxy) aniline derivative) were measured to investigate heat storage stability. The amount of the decomposition product is shown in Table 2.

TABLE 2

Decomposition product (wt. %) formed at 60° C.

| Sample | Time (month) | Decomposition product (wt. %) formed | | |
|---|---|---|---|---|
| | | Lot 1 | Lot 2 | Lot 3 |
| Invention crystal | 1 | 0.0 | 0.0 | 0.0 |
| | 2 | 0.0 | 0.0 | 0.0 |
| | 3 | 0.0 | 0.0 | 0.0 |
| First crystal | 1 | 0.1 | 0.0 | 0.0 |
| | 2 | 1.1 | 0.7 | 0.5 |
| | 3 | 2.1 | 1.5 | 1.4 |

As a result, a change in powder X-ray diffraction pattern showing transition of crystal was not recognized from any crystal. The first crystal formed about 1.7 wt. % of a decomposition product after 3-month storage, while no decomposition product appeared from the invention crystal even after 3 months, suggesting that the invention crystal has excellent heat storage stability.

Formulation Example 1: Tablets

| Formulation Example 1: Tablets | |
|---|---|
| Suplatast tosilate crystal (Example 1) | 50 mg |
| Corn starch | 50 mg |
| Microcrystalline cellulose | 50 mg |
| Hydroxypropyl cellulose | 15 mg |
| Lactose | 47 mg |
| Talc | 2 mg |
| Magnesium stearate | 2 mg |
| Ethyl cellulose | 30 mg |
| Unsaturated glyceride | 2 mg |
| Titanium dioxide | 2 mg |

The above-described ingredients in the proportions given were made into tablets, each 250 mg, in a conventional manner.

| Formulation Example 2: Granules | |
|---|---|
| Suplatast tosilate crystal (Example 1) | 300 mg |
| Lactose | 540 mg |

| Formulation Example 2: Granules | |
|---|---|
| Corn starch | 100 mg |
| Hydroxypropyl cellulose | 50 mg |
| Talc | 10 mg |

The above-described ingredients in the proportions given were made into granules, 1000 mg each package, in a conventional manner.

| Formulation Example 3: Capsules | |
|---|---|
| Suplatast tosilate crystal (Example 1) | 100 mg |
| Lactose | 30 mg |
| Corn starch | 50 mg |
| Microcrystalline cellulose | 10 mg |
| Magnesium stearate | 3 mg |

The above-described ingredients in the proportions given were made into capsules, each 193 mg, in a conventional manner.

| Formulation Example 4: Dry Syrups | |
|---|---|
| Suplatast tosilate crystals (Example 1) | 50 mg |
| Lactose · sucrose | 949 mg |
| Flavor | q.s. |

The above-described ingredients in the proportions given were made into dry syrups, each package containing 1000 mg, in a conventional manner.

| Formulation Example 5: Suppository | |
|---|---|
| Suplatast tosilate crystal (Example 1) | 300 mg |
| "Witepsol W-35" | 1400 mg |

(Trademark, a mixture of mono-, di- and triglyceride of saturated fatty acids from lauric acid to stearic acid, product of Dynamite Nobel Co., Ltd.)

The above-described ingredients in the proportions given were made into a suppository in a conventional manner.

INDUSTRIAL APPLICABILITY

Owing to merits such as a fluctuation-free optically active substance ratio, low hygroscopicity and high storage stability, the suplatast tosilate crystal of the present invention can be mass produced easily and at the same time, is advantageous in drug preparation and quality management. It is excellent as a raw material for pharmaceuticals such as medicaments for allergic diseases, dysuria and pruritus due to kidney dialysis.

The invention claimed is:

1. A suplatast tosilate crystal showing characteristic peaks in powder X-ray diffraction at diffraction angles (2θ±0.1°) of 5.6°, 9.0°, 11.0°, 15.3°, 16.5°, 17.2°, 17.9°, 19.2°, 19.9° and 21.5°.

2. A process for preparing a suplatast tosilate crystal of claim 1, which comprises crystallizing or re-crystallizing suplatast tosilate from an acetone-water mixed solvent or a C$_{2-4}$ aliphatic alcohol-water mixed solvent.

3. A process of claim 2, wherein a water content in the acetone-water mixed solvent or a C$_{2-4}$ aliphatic alcohol-water mixed solvent ranges from 0.3 to 15 V/V %.

4. A pharmaceutical composition comprising a suplatast tosilate crystal of claim 1.

5. A treating method of allergic diseases, dysuria or pruritus due to kidney dialysis, which comprises
administering an effective amount of a suplatast tosilate crystal of claim 1 to a patient in need thereof.

6. A process of claim 2, wherein the mixed solvent is 2-propanol, 2-butanol or acetone, with water.

7. A process of claim 2, wherein the mixed solvent is present in a concentration range of from 10 to 70 W/V %.

8. A process of claim 3, wherein the water content ranges from 0.5 to 12 V/V %.

9. A process of claim 3, wherein the water content ranges from 0.8 to 10 V/V %.

10. A process of claim 3, wherein the water content ranges from 1.5 to 3 V/V %.

11. A pharmaceutical composition of claim 4, additionally containing a steroid drug.

12. A method of reducing side effects in the treatment of chronic cystitis, interstitial cystitis or chronic prostitis, which comprises administering an effective amount of the pharmaceutical composition of claim 11 to a patient in need thereof.

* * * * *